(12) United States Patent
Krumme et al.

(10) Patent No.: US 7,880,569 B2
(45) Date of Patent: Feb. 1, 2011

(54) ROTATING DATA TRANSMISSION DEVICE

(75) Inventors: Nils Krumme, Feldafing (DE); Stephan Lindorfer, Munich (DE); Ulrich Bertl, Peiting (DE); Stefan Popescu, Erlangen (DE)

(73) Assignees: Schleifring und Apparatebau GmbH, Fuerstenfeldbruck (DE); Siemens Aktiengesellschaft, Munich (DE)

( * ) Notice: Subject to any disclaimer, the term of this patent is extended or adjusted under 35 U.S.C. 154(b) by 1113 days.

(21) Appl. No.: 11/560,286

(22) Filed: Nov. 15, 2006

(65) Prior Publication Data

US 2007/0152783 A1 Jul. 5, 2007

(51) Int. Cl.
*H01P 1/00* (2006.01)

(52) U.S. Cl. ...................... 333/245; 370/245

(58) Field of Classification Search ........... 370/245, 370/405, 401, 433, 463, 366, 509; 375/240.14, 375/260, 219
See application file for complete search history.

(56) References Cited

U.S. PATENT DOCUMENTS

| | | | |
|---|---|---|---|
| 5,027,352 A * | 6/1991 | Goode | 370/345 |
| 5,530,422 A | 6/1996 | Harrison | |
| 6,028,462 A * | 2/2000 | Kyles | 327/277 |
| 6,181,766 B1 | 1/2001 | Pearson, Jr. et al. | |
| 6,215,816 B1 * | 4/2001 | Gillespie et al. | 375/219 |
| 6,226,296 B1 * | 5/2001 | Lindsey et al. | 370/401 |
| 6,272,130 B1 * | 8/2001 | Panahi et al. | 370/366 |
| 6,538,656 B1 * | 3/2003 | Cheung et al. | 345/519 |
| 6,795,450 B1 * | 9/2004 | Mills et al. | 370/463 |
| 6,862,299 B2 | 3/2005 | Popescu | |
| 7,181,485 B1 * | 2/2007 | Lau et al. | 718/100 |
| 7,292,597 B2 * | 11/2007 | Mills et al. | 370/433 |
| 2001/0010694 A1 * | 8/2001 | Lindsey et al. | 370/405 |
| 2003/0086503 A1 * | 5/2003 | Rennert et al. | 375/260 |
| 2003/0161348 A1 * | 8/2003 | Mills et al. | 370/509 |
| 2004/0208245 A1 * | 10/2004 | MacInnis et al. | 375/240.15 |

* cited by examiner

*Primary Examiner*—Thong H Vu
(74) *Attorney, Agent, or Firm*—Kevin L. Daffer; Daffer McDaniel, LLP

(57) ABSTRACT

A rotating data transmission device for computer tomographs, for transmission from a rotating part to a stationary part that is rotatably supported relative to the rotating part, comprises at least a rotating high-speed data transmitter unit, a rotating high-speed transmission line, a stationary high-speed data receiver unit. The rotating high-speed data transmitter unit contains a rotating pattern controller and the stationary high-speed data receiver unit contains a stationary data analyzer for analyzing patterns generated by the rotating pattern controller. Furthermore unit controllers are provided to control the units.

21 Claims, 3 Drawing Sheets

ROTATING DATA TRANSMISSION DEVICE

PRIORITY CLAIM

The present application claims priority to German Application No. 102005054981.0 filed Nov. 16, 2005.

BACKGROUND OF THE INVENTION

1. Field of the Invention

The invention relates to a rotating data transmission device, in particular for use in computer tomographs. Here a transmission of digital image data obtained by an X-ray detector is effected in a non-contacting manner between a rotable gantry and a stationary part of a computer tomograph. Furthermore, data can also be transmitted in the opposite direction to control the rotable gantry.

2. Description of the Prior Art

A device for non-contacting rotating data transmission in computer tomographs is known from U.S. Pat. No. 5,530,422. In this, a signal to be transmitted is fed into a differentially operated strip conductor line on a rotating gantry, and is tapped off by a capacitive probe on the stationary part. Devices of this kind are usable up to data rates of an order of magnitude of approx. 1 GBaud. This limit may be shifted slightly to higher values by further developments, as disclosed for example in U.S. Pat. No. 6,181,766. For this, suitable encodings or modulation methods are employed. A further improvement can be achieved by using CDR (Clock and Data Recovery circuits) as disclosed in U.S. Pat. No. 6,862,299. Such CDRs can compensate for signal distortion caused by connecting lines or by the contactless data link itself.

BRIEF SUMMARY OF THE INVENTION

The invention is based on the object of improving prior art devices for non-contacting transmission of digital signals between two units that are movable relative to each other, and in particular between a stationary and a rotating part of a computer tomograph, so that a higher flexibility and the ability to transmit different data rates over the same data link can be maintained.

In accordance with the invention, this object is achieved by a rotating data transmission device for computer tomographs, for transmission from a rotating part that includes a transmitter for generating electrical signals to a stationary part that is rotatably supported relative to the rotating part and includes a receiver for receiving electrical signals. Said data transmission device comprises at least one contactless data link. The contactless data link has a least one transmitter for feeding electrical signals into at least one transmission line and at least one receiver for picking up and amplifying electrical signals from the transmission line. Typically in contactless data links the jitter is mainly deterministic, caused by bandwidth limiting of the electronic components as in the transmitter, the transmission line and the receiver. This jitter is removed or at least minimized by at least one CDR. Furthermore additional CDRs may be provided for example in the transmitter for reducing the transmitter's input jitter produced by the signal input line or an optical light wave guide delivering an input signal to the transmitter. Broadly speaking a CDR is re-clocking the serial data stream at its input. For this purpose an internal, stable clock of constant frequency with low jitter is generated by means of a PLL. This clock is compared with be input data stream and its frequency is adjusted, until it is equal to the clock frequency of the input data stream. The input data stream is re-synchronized or re-clocked with the PLLs internal stable clock. As a result the jitter of the re-clocked data stream corresponds to the relatively low jitter of the internal stable clock. In most cases the PLLs frequency is derived by means of a frequency divider from a Crystal oscillator resulting in a low jitter but also in a relatively narrow capture frequency range, where synchronization is possible. An adaptation to different data rates and therefore different clock frequencies is possible in many cases by modifying the frequency divider ratio and the PLL filter.

BRIEF DESCRIPTION OF THE DRAWINGS

In the following, the invention is described by way of example without limitation of the general inventive concept on examples of embodiment and with reference to the drawings.

DETAILED DESCRIPTION OF THE INVENTION

Figure 1:
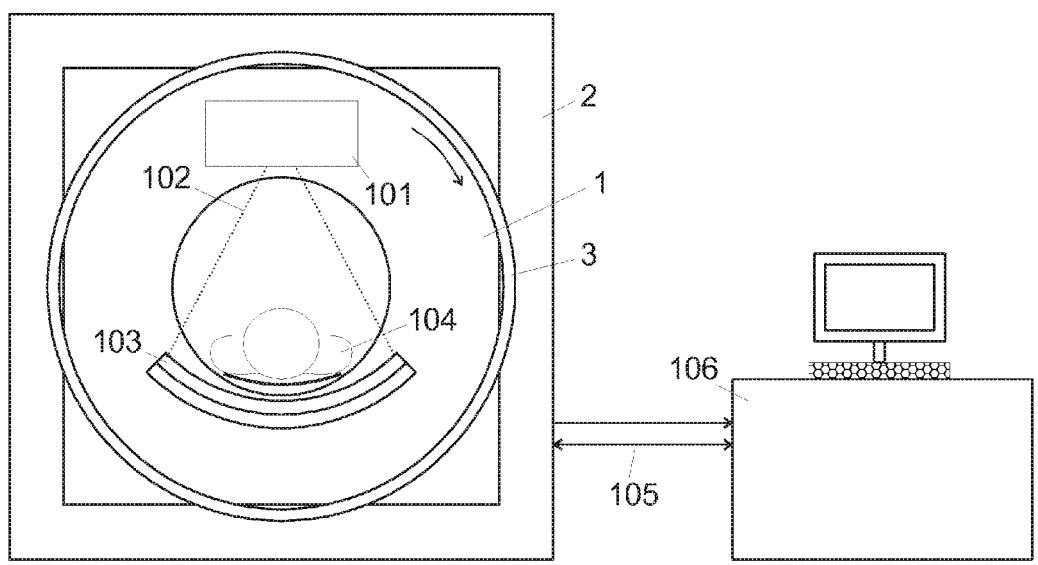
FIG. 1 shows by way of example a computer tomograph comprising a device in accordance with the invention.

FIG. 1 shows by way of example a device in accordance with the invention. The computer tomograph (CT scanner) consists of two main mechanical components. A stationary part 2 serves as a basis and a support for the entire instrument, in which the rotating part 1 rotates. A patient 104 is positioned on a berth inside the opening of the rotating part. An X-ray tube 101 and a detector 103 disposed opposite thereto are provided for scanning the patient by means of X-rays 102. The X-ray tube 101 and the detector 103 are rotatably disposed on the rotating part 1. A rotating data transmission device 3 serves as an electrical connection between the rotating part 1 and the stationary part 2. With this, high electrical power for feeding the X-ray tube 101 is transmitted in a direction towards the rotating part 1, and at the same time video data are transmitted in the opposite direction by means of a high speed data link. A communication of control information in both directions is provided in parallel with this. An evaluation and control unit 106 serves for operating the computer tomograph, and also for displaying generated images. Communication with the computer tomograph is effected via a bidirectional link 105.

Figure 2:
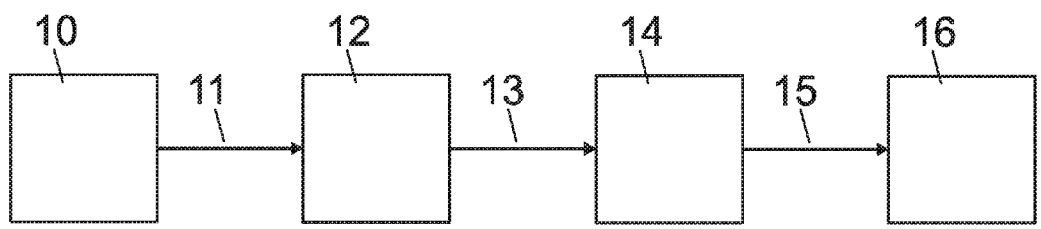
FIG. 2 shows schematically a device in accordance with the invention.

FIG. 2 shows by way of example a device according to the invention in detail. An inventive rotating data transmission device 3 comprises at least a rotating high-speed data transmitter unit 12, a rotating high-speed transmission line 13 and a stationary high-speed data receiver unit 14.

Data is generated by the data source unit 10, of which comprises a data source like a data acquisition system. This data is sent by a rotating part local data link 11 to the rotating high-speed data transmitter unit 12. The rotating part local data link 11 can be based on a light wave guide or on a copper cable, preferably a coaxial cable. The rotating high-speed data transmitter unit receives data from the data source unit and processes that data in such a way that it can be transferred to the stationary part. Such processing may include reconstruction, encoding, modulation or amplification. Such processed data is fed into the rotating high-speed transmission line 13, which usually spans around the circumference of said rotating part. On the stationary part a high speed data receiver 14 unit picks up that data from the rotating high-speed transmission line 13. Again data is processed therein. Such processing may include reconstruction, encoding, clock and data recovery (CDR), modulation or amplification. Also an error correction or error recovery may be provided. At processed data is forwarded to the data sink unit 16 by means of a stationary part local data link 15. This stationary part locate data link can be based on a light wave guide or on a copper cable, preferably a coaxial cable. The data sink unit may comprise a storage and/or a computer or processor to process the received data.

Figure 3:
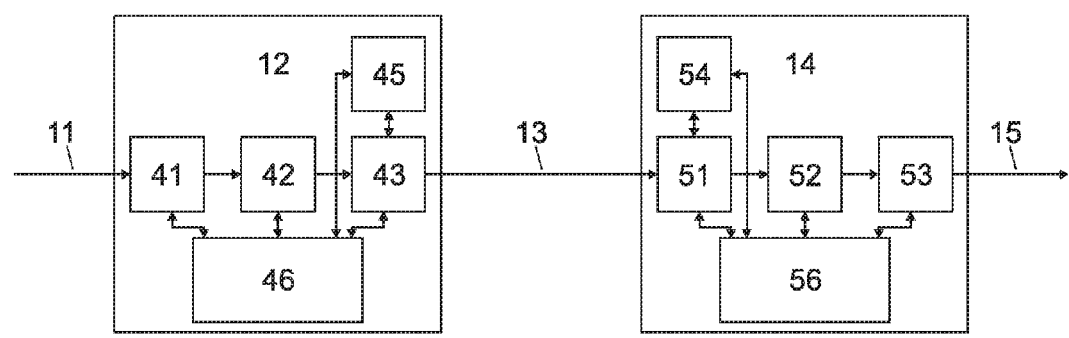
FIG. 3 shows a rotating data transmission device for computer tomographs.

FIG. 3 shows a rotating data transmission device 3 for computer tomographs. This rotating data transmission device comprises a rotating high speed data transmitter unit 12, a rotating high-speed data transmission line 13, and a stationary high-speed data receiver unit.

In this example the rotating high-speed data transmitter unit 12 comprises the following components: a local link receiver 41 for receiving data via a rotating part local data link; a rotating part clock and data recovery circuit 42, which receives data from the local link receiver 41 and reduces jitter of said data; a rotating high-speed data transmitter 43 which processes data from the rotating clock and data recovery circuit for sending these data over the rotating high-speed data transmission line 13; an optional rotating pattern generator 45 for generating at least one test pattern for the rotating high-speed data transmitter to be transmitted to the stationary part; a rotating high-speed data transmitter unit controller 46 which controls the rotating high-speed data transmitter unit, and which may therefore control the rotating local link receiver 41, the rotating clock and data recovery circuit 42, the rotating high-speed data transmitter 43 and the rotating pattern generator 45.

The high-speed data transmission line can be any line as known from prior art, preferably a strip line or a broad band filter line as disclosed in U.S. Pat. No. 6,956,450.

The stationary high-speed data receiver unit 14 comprises the following components: a stationary high-speed data receiver 51, which picks up data from the rotating high-speed transmission line; a stationary clock and data recovery circuit 52, which receives data from the high-speed data receiver 51 and reduces jitter thereof; a stationary part local data link transmitter 53 which sends data from the stationary clock and data recovery circuit 52 over the stationary part local data link 15; an optional stationary data analyzer 54 for analyzing data patterns received by the high-speed data receiver 51, alternatively for analyzing the re-clocked data from the stationary clock data recovery circuit 52; a stationary high-speed data receiver unit controller 56 which controls the stationary high-speed data receiver unit, and which may therefore control the stationary high-speed data receiver 51, the stationary clock and data recovery circuit 52, the stationary part local data link transmitter 53 and the stationary part data analyzer 54.

The stationary data analyzer 54 is preferably used together with the rotating pattern generator 45 to establish a test mode. In this test mode the rotating pattern generator 45 generates specific test patterns, which are analyzed by the stationary data analyzer 54. The result of this analysis may be used to calculate a bit error rate or any other parameter describing link quantity.

Figure 4:
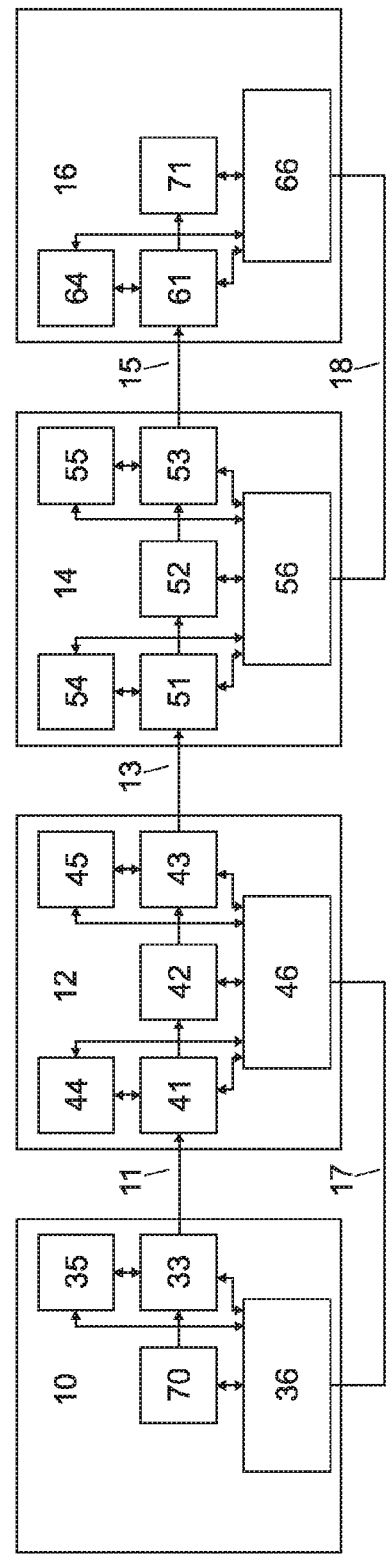
FIG. 4 shows a computer tomograph with a data transmission device.

FIG. 4 shows a computer tomograph with a rotating data transmission device. The rotating high-speed data transmitter unit 12, the rotating high-speed transmission line and the stationary high-speed data receiver unit are basically the same as described previously. Only a rotating local data analyzer 44 has been added in the rotating high-speed data transmitter unit 12 for analyzing data from the data source unit 10 and a stationary local pattern generator 55 has been added in of the stationary high-speed data receiver unit 13 for sending test patterns to the data sink unit 16.

Furthermore a data source unit 10 comprises a data source 70, which may be a data acquisition system, delivering data to the rotating part local data link transmitter 33. As described previously, test patterns, generated by the stationary local pattern generator 35 may be fed to the rotating part local data link transmitter 33, received by local link receiver 41 and evaluated by the rotating local data analyzer 54. Alternatively the rotating local data analyzer 54 may be connected to the rotating clock and data recovery circuit 42 for evaluating re-clocked signals. Preferably this rotating local data analyzer 54 analyzes specific test patterns generated by rotating pattern generator 45. It may be further designed to calculate or estimate any link quality parameter like the bit error rate. A data source controller 36 controls the data source unit and therefore preferably the data source 70, the stationary local pattern generator 35 and the rotating part local data link transmitter 33. The data source controller 36 is preferably connected via rotating part local control bus 17 to the rotating high-speed data transmitter unit controller 46. Optionally other devices may be connected to be rotating part local control bus 17.

A data sink unit 16 comprises a data sink 71 receiving data from a stationary part local link receiver 61 over the stationary part locate data link 15. Optionally the data sink 71 may contain a clock and data covering circuit. Furthermore an optional stationary local data analyzer 64 is provided for analyzing the data. Preferably this data analyzer analyzes specific test patterns from stationary local pattern generator 55. Furthermore it preferably estimates or calculates any link quality parameter.

A data sink controller 56 is provided for controlling the data sink unit. It therefore preferably controls the data sink 71, the stationary part local data link receiver 61 and the stationary local data analyzer 64. It is furthermore currently connected via stationary local control bus 18 to the stationary high-speed data receiver unit controller 56. Optionally other devices may be connected to be stationary part local control bus 18. Furthermore the rotating part local control bus 17 may be connected to be stationary part local control bus 18, preferably by an additional contactless data link or mechanical slip ring.

In a further embodiment of the invention at least one of said rotating high-speed data transmitter unit 12, data source unit 10 or stationary high-speed data receiver unit 14 comprises at least one pattern generator (35, 45, 55) for generating at least one test pattern, and at least one of said stationary high-speed data receiver unit 14, rotating high-speed data transmitter unit 12 or data sink unit 16 comprises at least one pattern analyzer (44, 54, 64) for analyzing at least one of said test patterns. The table below shows possible combinations of units containing pattern generators which are enabled for generating data patterns and units containing pattern analyzers being enabled for analyzing patterns.

| Pattern generator | Pattern analyzer |
| --- | --- |
| data source unit | rotating high-speed data transmitter unit |
| data source unit | stationary high-speed data receiver unit |
| data source unit | data sink unit |
| rotating high-speed data transmitter unit | stationary high-speed data receiver unit |
| rotating high-speed data transmitter unit | data sink unit |
| stationary high-speed data receiver unit | data sink unit |

It is not to be distinguished here between a data source 17 containing a pattern controller and any data source 17 being contained in the data source unit 10 together with a rotating local pattern generator 35. The same is valid for data sink 71, data sink unit 16 and a stationary local data analyzer 64.

In a further embodiment of the invention the data source controller 36 is configured to communicate with said rotating high-speed data transmitter controller 46 by inserting or modifying messages into said high speed data. Alternatively, the data sink controller 66 is configured to communicate with said stationary high-speed data receiver controller 56 by inserting or modifying messages into said high speed data. In a further alternative the rotating part local control bus 17 is configured to communicate with the stationary part local control bus 18 by inserting or modifying messages into the high speed data.

As a further alternative at least one of said data source controller 36, rotating high-speed data transmitter controller 46, stationary high-speed data receiver controller 56 and data sink controller 66 is configured to communicate with at least another of said controllers by means of at least one additional slipring or at least one additional high speed data link. The additional high-speed data link may also operate into the opposite direction of the first high-speed data link, e.g. from stationary part to rotating part.

Furthermore any one or several of said controllers may be controlled by or connected to an external controller or a master controller or a computer.

In another embodiment of the invention several of the controllers 36, 46, 56 and 66 have unique interfaces to communicate with each other.

In another embodiment of the invention at least one of these controllers is configured to store configuration parameters for attached devices and to recall these parameters and forward them to be attached devices upon an external command or power up.

In a further embodiment of the invention at least one of said rotating high-speed data transmitter unit, said rotating high-speed transmission line or said stationary high-speed data receiver unit, is configured to automatically detect the data rate signals received by its receiver.

In a further embodiment of the invention the rotating high-speed data transmitter unit 12 and the stationary high-speed data receiver unit 14 are configured to enter a diagnostics mode upon an external control signal or command, where test patterns are generated and analyzed. An external control signal or command may be issued by any of said controllers or by an external controller. Alternatively the data source unit 10 and said rotating high-speed data transmitter unit 12 are configured to enter a diagnostics mode upon an external control signal or command, where test patterns are generated and analyzed. In a further alternative the stationary high-speed data receiver unit 14 and said data sink unit 16 are configured to enter a diagnostics mode upon an external control signal or command, where test patterns are generated and analyzed. Furthermore at least one of said rotating high-speed data transmitter unit 12, data source unit 10 or stationary high-speed data receiver unit 14, and at least one of said stationary high-speed data receiver unit 14, rotating high-speed data transmitter unit 12 or data sink unit 16 may be configured to enter a diagnostics mode upon an external control signal or command, where test patterns are generated and analyzed.

A method for transmission of high-speed data generated by a data source on a rotating part of a computer tomography scanner to a data sink on a stationary part comprises the following steps: receiving data from the data source by a rotating part local link receiver; re-clocking said data by means of a clock and data recovery circuit; sending said re-clocked data to a rotating high-speed transmission line by a rotating high-speed data transmitter; receiving said data from said rotating high-speed transmission line by means of a stationary high-speed data receiver; re-clocking said received data by means of a clock and data recovery circuit; transmitting said re-clocked data to said data sink by a stationary part local link transmitter; it further comprises at least one of the steps: controlling and configuring at least a clock and data recovery circuit on the rotating part and/or said rotating high-speed data transmitter; and controlling and configuring at least a clock and data recovery circuit on the stationary part and/or said stationary high-speed data receiver.

To simplify the explanations, repeated reference will be made in the following to a transmission from the rotating part to the stationary part of a computer tomograph. Of course, a device in accordance with the invention may also be used in the opposite direction of transmission. Similarly, a device in accordance with the invention may also be utilized in other applications of rotary transmission, and similarly for linear transmission between two units that are movable relative to each other.

The invention claimed is:

1. Rotating data transmission device for computer tomographs, for transmission of high speed data generated by a data source on the rotating part to a stationary part that is rotatably supported relative to the rotating part and includes a data sink for receiving electrical signals, having a rotating high speed data transmitter unit for feeding high-speed data from said data source into a rotating high speed transmission line, and a stationary high speed data receiver unit for receiving said high speed data from said high speed transmission line and forwarding the received data to said data sink, wherein said rotating high speed data transmitter unit comprises:
   at least one rotating part local link receiver for receiving data from the data source;
   at least one clock and data recovery circuit for re-synchronizing data received by said at least one local link receiver;
   at least one rotating high speed data transmitter for sending re-synchronized signals to the rotating high-speed transmission line; and
   at least one controller for controlling and configuring said rotating high-speed data transmitter unit;
   wherein said stationary high speed data receiver unit comprises:
   at least one stationary high speed data receiver for taking up data from said rotating high-speed transmission line;
   at least one clock and data recovery circuit for re-synchronizing data received by said at least one stationary high speed data receiver;
   at least one stationary clock local link transmitter for sending data over a stationary part local data link to said data sink; and
   at least one controller for controlling and configuring said stationary high speed data receiver units.

2. Computer tomography scanner comprising:
   a rotating part with a data source unit for generating high-speed imaging data, a rotating data transmission device for transmission of said high speed data to a stationary part; said rotating part having a rotating high speed data transmitter unit for feeding high-speed data from said data source unit into a rotating high speed transmission line; and a stationary part that is rotatably supported relative to the rotating part and includes a data sink unit for receiving electrical signals and said stationary part having a stationary high speed data receiver unit for receiving said high speed data from said high speed transmission line and forwarding the received data to said data sink unit;

wherein said data source unit comprises:
at least one data source; and
at least one rotating part local data link transmitter;

said rotating high speed data transmitter unit comprises:
at least one rotating part local link receiver for receiving data from the data source;
at least one clock and data recovery circuit for re-synchronizing data received by said at least one local link receiver;
at least one rotating high speed data transmitter for sending re-synchronized signals to the rotating high-speed transmission line; and
at least one rotating high-speed data transmitter controller for controlling and configuring rotating high-speed data transmitter unit;

said stationary high speed data receiver unit comprises:
at least one stationary high speed data receiver for taking up data from said rotating high-speed transmission line;
at least one clock and data recovery circuit for re-synchronizing data received by said at least one stationary high speed data receiver;
at least one stationary clock local link transmitter for sending data over a stationary part local data link to said data sink; and
at least one stationary high speed data receiver controller for controlling and configuring said stationary high speed data receiver unit; and said data sink unit comprises:
at least one stationary part local data link receiver; and
at least one data sink.

3. Device according to claim 1 or 2, wherein said rotating high-speed data transmitter unit comprises at least one pattern generator being controlled by said rotating high-speed data transmission unit controller, and said stationary high-speed data receiver unit comprises at least one pattern analyzer being controlled by said stationary high-speed data transmission unit controller.

4. Device according to claim 3, wherein said rotating high-speed data transmitter unit and said stationary high-speed data receiver unit are configured to enter a diagnostics mode upon an external control signal or command, where test patterns are generated and analyzed.

5. Device according to claim 2, wherein said data source unit comprises a data source controller and at least one pattern generator being controlled by said data source controller, and said rotating high-speed data transmitter unit comprises at least one data analyzer being controlled by said rotating high-speed data transmitter controller.

6. Device according to claim 5, wherein said data source controller is connected to a said rotating high-speed data transmitter controller by a rotating part local control bus.

7. Device according to claim 5, wherein said data source controller is configured to communicate with said rotating high-speed data transmitter controller by inserting or modifying messages into said high speed data.

8. Device according to claim 5, wherein said data source unit and said rotating high-speed data transmitter unit are configured to enter a diagnostics mode upon an external control signal or command, where test patterns are generated and analyzed.

9. Device according to claim 2, wherein said stationary high-speed data receiver unit comprises at least one pattern generator being controlled by stationary high-speed data receiver controller, and wherein said data sink unit comprises a data sink controller and at least one pattern analyzer being controlled by said data sink controller.

10. Device according to claim 9, wherein said data sink controller is connected to a said stationary high-speed data receiver controller by a stationary part local control bus.

11. Device according to claims 6 or 10, wherein said rotating part local control bus is connected to said stationary clock local control bus.

12. Device according to claims 6 or 10, wherein said rotating part local control bus is configured to communicate with said stationary clock local control bus by inserting or modifying messages into said high speed data.

13. Device according to claims 3, 5, 6 or 10, wherein at least one of said data source controller, rotating high-speed data transmitter controller, stationary high-speed data receiver controller and data sink controller is configured to communicate with at least another of said controllers by means of at least one additional slipring or at least one additional high speed data link.

14. Device according to claim 9, wherein said data sink controller is configured to communicate with said stationary high-speed data receiver controller by inserting or modifying messages into said high speed data.

15. Device according to claim 9, wherein said stationary high-speed data receiver unit and said data sink unit are configured to enter a diagnostics mode upon an external control signal or command, where test patterns are generated and analyzed.

16. Device according to claim 2, wherein at least one of said rotating high-speed data transmitter unit, data source unit or stationary high-speed data receiver unit comprises at least one pattern generator for generating at least one test pattern, and wherein at least one of said stationary high-speed data receiver unit, rotating high-speed data transmitter unit or data sink unit comprises at least one pattern analyzer for analyzing at least on of said test patterns.

17. Device according to claim 16, wherein at least one of said rotating high-speed data transmitter unit, data source unit or stationary high-speed data receiver unit, and wherein at least one of said stationary high-speed data receiver unit, rotating high-speed data transmitter unit or data sink unit are configured to enter a diagnostics mode upon an external control signal or command, where test patterns are generated and analyzed.

18. Device according to claims 1 or 2, wherein said controllers have a unique interface to communicate with each other.

19. Device according to claims 1 or 2, wherein at least one of said controllers is configured to store configuration parameters for attached devices and to recall these parameters and forward them to the attached devices upon an external command or power up.

20. Device according to claims 1 or 2, wherein at least one of said rotating high-speed data transmitter unit or said stationary high-speed data receiver unit, is configured to automatically detect the data rate signals received by its receiver.

21. Method for transmission of high-speed data generated by a data source on a rotating part of a computer tomography scanner to a data sink on a stationary part comprising the following steps:
receiving data from the data source by a rotating part local link receiver;
re-clocking said data by means of a clock and data recovery circuit;

sending said re-clocked data to a rotating high-speed transmission line by a rotating high-speed data transmitter;
receiving said data from said rotating high-speed transmission line by means of a stationary high-speed data receiver;
re-clocking said received data by means of a clock and data recovery circuit;
transmitting said re-clocked data to said data sink by a stationary part local link transmitter; and further comprising at least one of the steps:
controlling and configuring at least a clock and data recovery circuit on the rotating part and/or said rotating high-speed data transmitter; and
controlling and configuring at least a clock and data recovery circuit on the stationary part and/or said stationary high-speed data receiver.

* * * * *

UNITED STATES PATENT AND TRADEMARK OFFICE
CERTIFICATE OF CORRECTION

| | | |
|---|---|---|
| PATENT NO. | : 7,880,569 B2 | Page 1 of 1 |
| APPLICATION NO. | : 11/560286 | |
| DATED | : February 1, 2011 | |
| INVENTOR(S) | : Krumme et al. | |

It is certified that error appears in the above-identified patent and that said Letters Patent is hereby corrected as shown below:

Claim 16 at col. 8, line 39: After "at least" please delete "on" and substitute --one--.

Signed and Sealed this
Twenty-first Day of June, 2011

David J. Kappos
*Director of the United States Patent and Trademark Office*